United States Patent [19]
Carmody

[11] Patent Number: 5,145,685
[45] Date of Patent: Sep. 8, 1992

[54] SKIN TREATMENT METHOD AND COMPOSITION

[75] Inventor: Walter J. Carmody, Port Jervis, N.Y.

[73] Assignee: Dow Corning Corporation, Midland, Mich.

[21] Appl. No.: 682,056

[22] Filed: Apr. 8, 1991

[51] Int. Cl.⁵ .......................... A61K 9/50; A61K 7/35
[52] U.S. Cl. ........................... 424/501; 424/69; 424/489; 424/401
[58] Field of Search ............. 424/81, 484, 486, 78, 424/489, 501, 69, 401

[56] References Cited

U.S. PATENT DOCUMENTS

| Re. 33,429 | 11/1990 | Abrutyn | 514/847 |
|---|---|---|---|
| 4,076,622 | 2/1978 | Costin | 424/79 |
| 4,690,825 | 9/1987 | Won | 424/501 |
| 4,719,040 | 1/1988 | Traas | 512/4 |
| 4,724,240 | 2/1988 | Abrutyn | 514/847 |
| 4,764,362 | 8/1988 | Barchas | 424/61 |
| 4,776,358 | 10/1988 | Korsk | 132/321 |
| 4,806,360 | 2/1989 | Leong | 424/487 |
| 4,813,976 | 3/1989 | Barchas | 51/293 |
| 4,828,542 | 5/1989 | Hermann | 604/3 |
| 4,855,127 | 8/1989 | Abrutyn | 424/411 |
| 4,855,144 | 8/1989 | Leong | 424/487 |
| 4,870,145 | 9/1989 | Chromecek | 526/217 |
| 4,873,091 | 10/1989 | Jankower | 424/489 |
| 4,880,617 | 11/1989 | Chromecek | 424/501 |
| 4,881,490 | 11/1989 | Ducharme | 119/1 |
| 4,883,021 | 11/1989 | Ducharme | 119/1 |
| 4,898,913 | 2/1990 | Ziemelis | 525/301 |
| 4,904,524 | 2/1990 | Yoh | 428/311 |
| 4,923,894 | 5/1990 | Kanda | 514/493 |
| 4,933,372 | 6/1990 | Feibush | 521/91 |
| 4,948,818 | 8/1990 | Carmody | 521/149 |
| 4,958,999 | 9/1990 | Liscomb | 425/110 |
| 4,961,532 | 10/1990 | Tangney | 239/60 |
| 4,962,133 | 10/1990 | Chromecek | 521/56 |
| 4,962,170 | 10/1990 | Chromecek | 526/212 |
| 5,035,885 | 7/1991 | Arraudeau et al. | 424/78 |
| 5,035,886 | 7/1991 | Chakrabarti et al. | 424/78 |

FOREIGN PATENT DOCUMENTS

| 1168157 | 5/1984 | Canada . |
|---|---|---|
| 61701 | 10/1982 | European Pat. Off. . |
| 306236 | 3/1989 | European Pat. Off. . |
| 369741 | 5/1990 | European Pat. Off. . |
| 8702013 | 2/1988 | PCT Int'l Appl. . |
| 8910132 | 11/1989 | PCT Int'l Appl. . |

*Primary Examiner*—Thurman K. Page
*Assistant Examiner*—Peter F. Kulkosky
*Attorney, Agent, or Firm*—Jim L. DeCesare

[57] ABSTRACT

A method of treating skin disorders such as acne by applying topically to the infected area a mixture of an antimicrobial agent and a volatile low viscosity organosilicon compound. The mixture is entrapped within and dispersed uniformly throughout discrete particles of a hydrophobic macroporous highly crosslinked polymer. The particles are spread on the skin releasing the mixture while allowing the volatile low viscosity organosilicon compound to evaporate. Excess skin oil such as sebum is simultaneously adsorbed from the skin and into the macroporous polymer.

20 Claims, 3 Drawing Sheets

1500X

10000X

2000X

1500X

10000X

SKIN TREATMENT METHOD AND COMPOSITION

BACKGROUND OF THE INVENTION

This invention relates to a method of treating human skin and more particularly is directed to the alleviation of acne by applying to the infected area a mixture of an antimicrobial agent and a volatile cyclic silicone. The mixture is delivered to the skin by entrapping the mixture within particles of a hydrophobic macroporous highly cross-linked polymer.

The concept of producing spheres and beads of a macroporous polymer is old in the art as is the use of such macroporous structures for the entrapment and subsequent delivery of certain active ingredients. One example of this concept may be found in U.S. Pat. No. 4,690,825 issued Sep. 1, 1987 in which a suspension polymerization process is employed to produce beads from a monomer system including styrene and divinylbenzene. Mineral oil is entrapped "in situ" and the beads are stated to possess utility in various cosmetic applications. In U.S. Pat. No. 4,719,040 issued Jan. 12, 1988 a macroporous polymer laden with perfume is incorporated into an air freshener gel. U.S. Pat. No. Re. 33,429 issued Nov. 6, 1990; European Patent 61,701 granted Jul. 16, 1986; and Canadian Patent 1,168,157 issued May 29, 1984; each relate to "in situ" entrapped moisturizers carried within macroporous beads. Various cosmetic and toiletry applications of these products are also disclosed.

A macroporous polymer entrapping an emollient is taught in U.S. Pat. No. 4,764,362 issued Aug. 16, 1988 and in U.S. Pat. No. 4,813,976 issued Mar. 21, 1989, in which the polymer is incorporated into a nail conditioning emery board. During filing of the nails, the emollient is released in order to condition and lubricate the nails. A similar concept is taught in U.S. Pat. No. 4,776,358 issued Oct. 11, 1988 in which a dental floss includes flavor oils entrapped in certain "microsponges". Suspension polymerized macroporous polymer beads are taught in U.S. Pat. No. 4,806,360 issued Feb. 21, 1989 and in U.S. Pat. No. 4,855,144 issued Aug. 8, 1989, wherein melanin pigment is incorporated into the macroporous structure and applied to the skin to function as a sunscreen. Similar bead structures are also taught in European application 306 236 published Mar. 3, 1989 and in Patent Cooperation Treaty International application WO 88/01164 published Feb. 25, 1988. Beads carrying a cationic charge in order to improve the adhesion to hair and skin are described in European application 369 741 published May 23, 1990.

A reticulated polyurethane foam is disclosed in U.S. Pat. No. 4,828,542 issued May 9, 1989 having macroporous polymer particles bonded to the foam. The particles entrap a liquid soap and the foam functions as a cleaning pad. In U.S. Pat. No. 4,855,127 issued Aug. 8, 1989 and U.S. Pat. No. 4,880,617 issued Nov. 14, 1989, hydrophobic polymeric porous beads are used as a free-flowing solid carrier for various pheromones, pesticides, fragrances and chemicals entrapped therein. Hydrophilic beads are formed in U.S. Pat. No. 4,870,145 issued Sep. 26, 1989 and upon removal of the solvent used to form voids, the beads possess various utilities such as incorporation into contact lens cleaners, facial scrubs and tile cleaners. In U.S. Pat. No. 4,873,091 issued Oct. 10, 1989 resilient microbeads are formed by suspension polymerizing curable elastomers such as isoprene rubbers to produce porous rubber beads. The porous rubber beads are employed in topical applications. In the Patent Cooperation Treaty International application WO89/10132 published Nov. 2, 1989 porous particles are disclosed as an ingredient in personal care emulsions. A pet litter is described in U.S. Pat. No. 4,881,490 issued Nov. 21, 1989 and U.S. Pat. No. 4,883,021 issued Nov. 28, 1989, wherein a macromolecular polymer entrapping a fragrance is incorporated into an animal litter to slowly release fragrance for combating odors.

In U.S. Pat. No. 4,898,913 issued Feb. 6, 1990 macroporous hydrophobic powder materials are rendered hydrophilic by treatment of the surface of the powder. In one embodiment of the '913 patent, the surface is saponified whereas in another embodiment an acrylate monomer is polymerized on the surface. A wet wipe useful in personal care applications is disclosed in U.S. Pat. No. 4,904,524 issued Feb. 27, 1990 wherein macroporous polymeric beads containing a silicone skin conditioner are incorporated into the surface of a paper sheet. Polymeric microparticles loaded with a fungicide are taught in U.S. Pat. No. 4,923,894 issued May 8, 1990. In U.S. Pat. No. 4,933,372 issued Jun. 12, 1990 there is described rigid resin particles formed by polymerizing monounsaturated and polyunsaturated monomers within the pores of inorganic template particles such as silica gel, silica, alumina, zirconia and metal oxides. The template particles are dissolved leaving porous adsorptive particles which mirror the template particles in size, surface area and porosity. Macroporous particles capable of adsorbing hydrophilic as well as lipophilic fluids are taught in U.S. Pat. No. 4,948,818 issued Aug. 14, 1990. Similar materials can be provided in bulk form as polymerized plugs containing entrapped pheromones in accordance with apparatus described in U.S. Pat. No. 4,958,999 issued Sep. 25, 1990. A fragrance dispenser device in the shape of an hourglass containing reticulate particulates entrapping an aroma chemical is depicted in U.S. Pat. No. 4,961,532 issued Oct. 9, 1990. In U.S. Pat. No. 4,962,133 issued Oct. 9, 1990 a process for producing macroporous particulates is described including the the inclusion of an azeotrope to enable an inorganic initiator to be employed. The '133 patent also contains a review of the prior art, a comprehensive list of the uses of such materials, and functional and active ingredients which may be entrapped therein. Similar materials produced by polymerizing only polyunsaturated monomers are set forth in U.S. Pat. No. 4,962,170 issued Oct. 9, 1990.

In accordance with the present invention however, a new and novel combination including such materials as a carrier has been discovered wherein provision is made for excess skin oil adsorption into the materials in addition to contact of the skin with entrapped acne treatment ingredients. The macroporous particles have been found to function as a skin oil absorbent when delivered in combination with a volatile cyclic silicone and an antimicrobial agent.

SUMMARY OF THE INVENTION

The invention is directed to a method of treating skin disorders by applying topically to the skin a mixture of an antimicrobial agent and a volatile low viscosity organosilicon compound. The mixture is entrapped within and dispersed uniformly throughout discrete particles of a hydrophobic macroporous highly crosslinked polymer. The particles are spread on the skin in order to release the mixture while allowing the volatile low viscosity organosilicon compound to evaporate. Excess skin oil such as sebum is adsorbed from the skin and into the macroporous polymer. The invention is also directed to a composition which is a mixture of the antimicrobial agent and the volatile cyclic silicone entrapped withing the polymer particles.

These and other objects, features, and advantages, of the present invention will become apparent when considered in light of the following detailed description including the accompanying drawings.

IN THE DRAWINGS

Each figure indicates in the upper left hand corner the magnification employed in producing the photomicrograph.

DETAILED DESCRIPTION OF THE INVENTION

Figure 1:
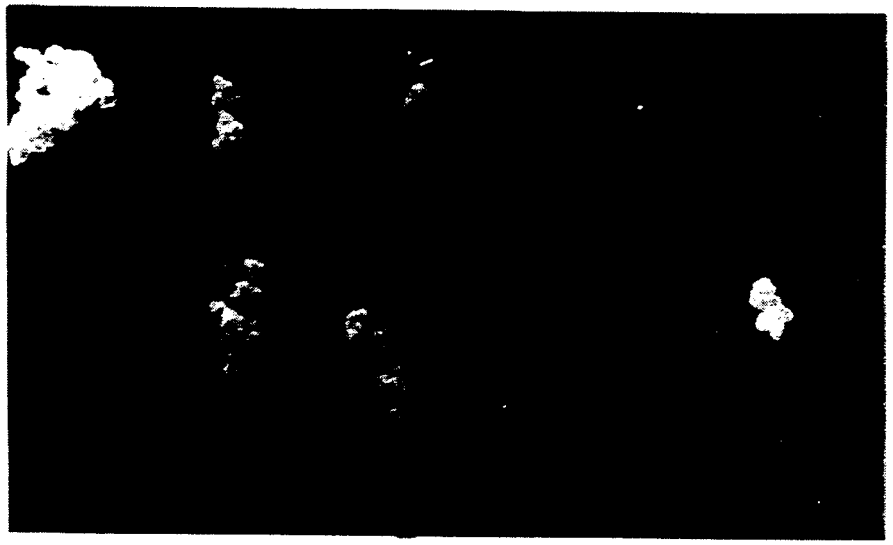
FIG. 1 is a photomicrograph showing the individual components of the complex structure of the macroporous powder which is produced by the precipitation polymerization process of Example I. There is illustrated the unit particles, agglomerates and aggregates which make up the powder.
Figure 2:
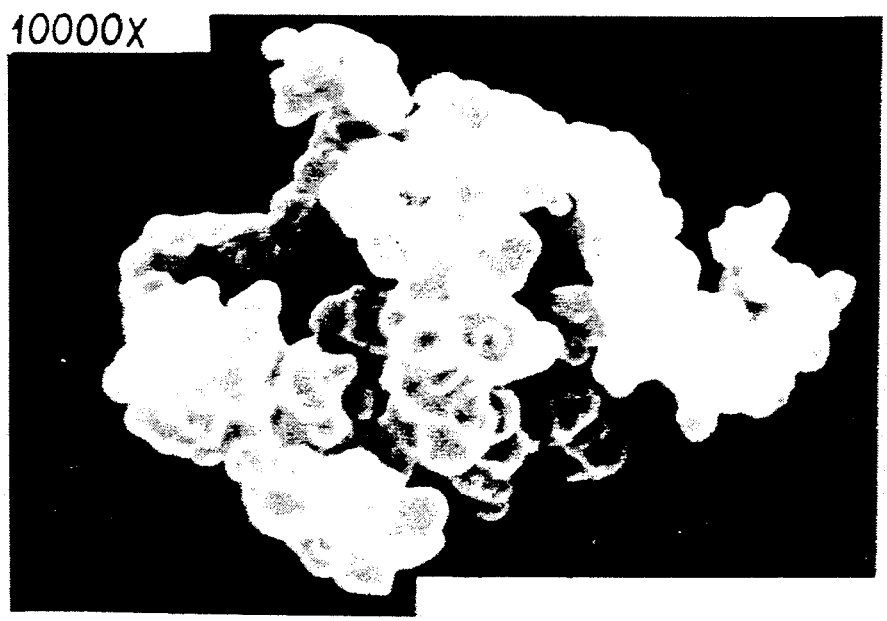
FIG. 2 is a photomicrograph of a single agglomerate of FIG. 1 but showing the agglomerate on an increased scale.
Figure 3:
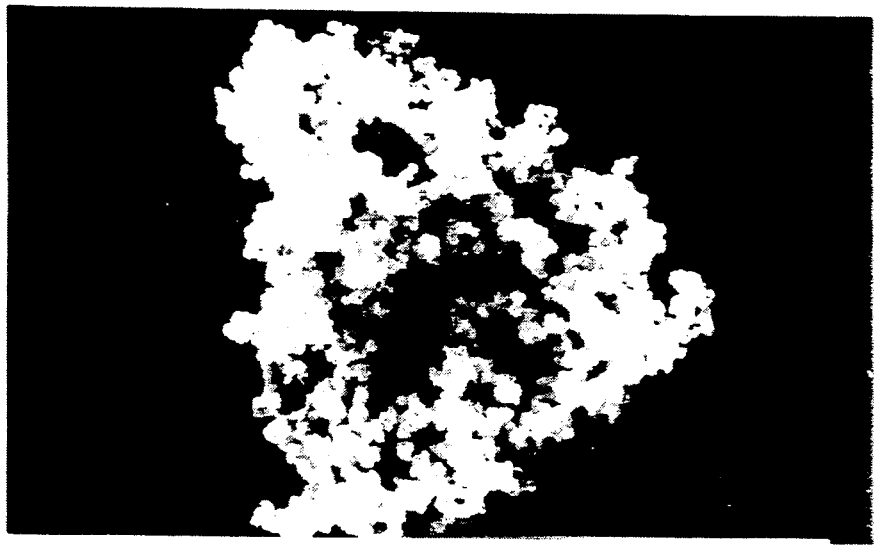
FIG. 3 is a photomicrograph of a single aggregate of FIG. 1 but showing the aggregate on an increased scale.

As should be apparent from a consideration of FIGS. 1-3, one embodiment of the polymeric material of the present invention is macroporous because of its complex arrangement of unit particles, agglomerates and aggregates. As a result of this complex structure the material possesses an inordinate proportion of interstitial space and is a labyrinth of voids. Volatile ingredients entrapped within the void volume of the material are released by wicking to the surface and evaporate at a rate dependent upon such factors as temperature, vapor pressure and surface area. Nonvolatile ingredients migrate to the surface by means of capillary action and are released on contact with another surface. Mechanical disruption may also be used to release an entrapped ingredient. While the material is shear sensitive it is not compression sensitive. The materiaal is capable of wicking ingredients from another surface in the fashion of a sponge. The material does not shrink or expand even though it is capable of adsorbing several times its own weight of an active ingredient. Since the process involved is adsorption in contrast to absorption, the properties of both the material and the active ingredient are not altered. Active ingredients are entrapped within the material in contrast to being encapsulated. Encapsulation connotes a complete enclosing of one material within another such as a shell formed around a core of liquid. Encapsulated ingredients are released by mechanical disruption of the shell or dissolution of the shell, and once the shell is disrupted the entire contents of the shell are extracted. With entrapment however the release of the entrapped ingredient is controlled or sustained by wicking, evaporation and capillary action. In addition the active ingredient is permitted a relatively unobstructed ingress and egress into and out of the labyrinth of voids.

The hydrophobic macroporous material of the present invention can be generically described as a crosslinked polymer in particulate form capable of entrapping solids and liquids. The particles are free flowing and discrete particulates even when loaded with an active ingredient. One polymer representative of the materials in accordance with the present invention has the formula:

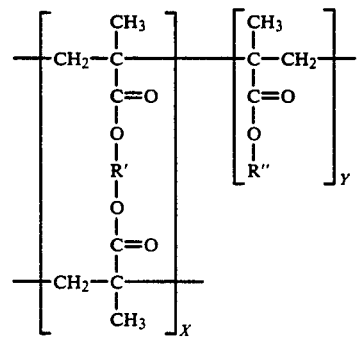

wherein the ratio of x to y is 80:20, R' is —CH$_2$CH$_2$—, and R" is —(CH$_2$)$_{11}$CH$_3$.

This polymeric material is highly crosslinked and is a polymethacrylate. The material is manufactured by the Dow Corning Corporation, Midland, Mich. and sold under the trademark POLYTRAP. It is a low density, highly porous free-flowing white particulate. The particles are capable of adsorbing high levels of lipophilic liquids and some hydrophilic liquids while at the same time maintaining a free-flowing particulate character. The polymer can be formed by polymerizing a single polyunsaturated monomer such as ethylene glycol dimethacrylate or tetraethylene glycol dimethacrylate. Such a process is described in U.S. Pat. No. 4,962,170 issued Oct. 9, 1990 which is incorporated herein by reference. The polymer may also be formed by polymerizing two monomers including a polyunsaturated monomer and a monounsaturated monomer such as lauryl methacrylate or 2-ethylhexyl methacrylate.

Depending upon which process for making the material is employed, the polymer particles can be in the form of a bead having an average diameter of about ten microns to about one hundred-fifty microns, or alternatively the polymer can be in the form of a powder. The powder form is best defined as a combined system of particles. The system of powder particles includes unit particles of less than about one micron in average diameter, agglomerates of many fused unit particles of sizes in the range of about twenty to eighty microns in average diameter, and aggregates of clusters of many fused agglomerates of sizes in the range of about two-hundred to about twelve-hundred microns in average diameter. Whether the polymer is in the form of a spherical macroporous bead or in the form of the complex macroporous powder, the structure is adapted to contain entrapped active materials depending upon the application.

A precipitation polymerization process is one method for producing the macroporous cross-linked polymer.

In the process there is polymerized one monounsaturated monomer and one polyunsaturated monomer in the presence of an excess of a volatile organic liquid which is a solvent for the monomers but not for the polymer. Polymerization of the monomers is initiated by means of a free radical generating catalytic compound which precipitates a polymer in the solvent in the form of a powder structure. A dry powder is formed by removing the volatile solvent from the precipitated polymeric powder leaving a structured submicron sized adsorbent. The most preferred solvent is isopropyl alcohol although other solvents such as ethanol, toluene, heptane, xylene, hexane, ethyl alcohol and cyclohexane may also be employed. The monounsaturated monomer and the polyunsaturated monomer can be present in various mole ratios such as 20:80, 30:70, 40:60, or 50:50. The process includes the step of stirring the monomers, solvent and the free radical generating catalytic compound during polymerization. The powder is dried by filtering excess solvent from the precipitated powder and the filtered powder is vacuum dried. The empty powder may be used in its dry form in some applications or it can be formulated by "post adsorbing" the empty powder with various functional materials.

Adsorption of active ingredients can be accomplished using a stainless steel mixing bowl and a spoon. The active ingredient is added to the empty dry powder and the spoon is used to gently fold the active into the powder. Low viscosity fluids may be adsorbed by addition of the fluids to a sealable vessel containing the powder and tumbling the materials until the desired consistency is achieved. More elaborate blending equipment such as ribbon or twin cone blenders can also be employed.

The following example illustrates one method of making an adsorbent powder of the type illustrated in FIGS. 1-3.

EXAMPLE I

A hydrophobic porous polymer was produced in a five hundred milliliter reactor equipped with a paddle type stirrer by mixing 13.63 grams of ethylene glycol dimethacrylate monomer or eighty mole percent and 4.37 grams of lauryl methacrylate monomer or twenty mole percent. Isopropyl alcohol was added to the reactor as the volatile solvent in the amount of 282 grams. The monomers were soluble in the solvent but not the precipitated polymer. The process can also be conducted using one polyunsaturated monomer as noted above. The mixture including the monomers, solvent and 0.36 grams of the catalytic initiator benzoyl peroxide was purged with nitrogen. The system was heated with a water bath to sixty degrees Centigrade until polymerization was initiated and the temperature was increased to 70-75 degrees for six hours to complete polymerization. During this time the polymer precipitated from the solution. The polymerization produced unit particles of a diameter less than about one micron. Some of the unit particles adhered and fused together forming agglomerates about twenty to eighty microns in diameter. Some of the agglomerates adhered and fused together forming aggregates of loosely held assemblies of agglomerates about two hundred to twelve hundred microns in diameter. The mixture was filtered to remove excess solvent and a wet powder cake was tray dried in a vacuum oven. A dry hydrophobic polymeric powder consisting of unit particles, agglomerates and aggregates was isolated.

The method of Example I is a precipitation polymerization technique. In accordance with this technique monomers are dissolved in a compatible volatile solvent in which both monomers solubilize. Polymer in the form of a powder is precipitated and the polymer is insoluble in the solvent. No surfactant or dispersing aid is required. The materials produced are randomly shaped particles and not spheres or beads. The randomly shaped powder particulates include unit particles, agglomerates and aggregates. The volatile solvent is removed leaving an empty dry powder. The empty dry powder is suitable for use in an active-free condition for some applications or it may be "post adsorbed" with a variety of functional active ingredients for other applications.

Some unique features of the powder of Example I and FIGS. 1-3 is its ability to adsorb liquids and yet remain free flowing. The material provides a regulated release of ingredients entrapped therein and has the capability of functioning as a carrier. The powders disappear when rubbed upon a surface. This phenomenon is due to the fact that large aggregates of the material scatter light rendering the appearance of a white particulate but when rubbed, these shear sensitive large aggregates decrease in size approaching the range of visible light and seem to disappear. The materials possess utility in many diverse areas such as the cosmetics and toiletries industry, household and industrial applications, agriculture as pesticide and pheromone carriers, and pharmaceuticals applications.

The following example illustrates another precipitation polymerization process in which an organic ester is entrapped "in situ" in the polymer. No volatile solvent is employed in Example II. The ester remains entrapped in accordance with this example.

EXAMPLE II

Seven grams of the ester 2-ethylhexyl oxystearate was mixed with 1.5 grams of ethylene glycol dimethacrylate and 1.5 grams of lauryl methacrylate in a glass test tube. The solution was deaerated for five minutes and 0.1 milliliters of t-butyl peroctoate was added and mixed while heating to eighty degrees Centigrade in an oil bath. After twenty minutes the contents of the glass test tube solidified and the mixture was maintained at the same temperature for an additional hour to assure full polymerization. A heterogeneous white polymer resulted containing the entrapped ester.

The powder product of Example I differs from the product of Example II in that a volatile solvent is used in Example I and the solvent is removed which results in a dry empty powder free of active ingredients. In Example II a non-volatile functional material is polymerized "in situ" and the active ingredient remains entrapped in the powder product.

In contrast to either of the previous examples, suspension polymerization is a process which is carried out in water. The monomers, active ingredient and the catalyst are combined and form beads or droplets in water and polymerization occurs within each bead. A surfactant and stabilizer such as polyvinyl pyrrolidone is required to prevent individually formed beads and droplets from coalescing. The resulting beads with the active material entrapped have a substantially spherical outer crust or shell and an interior macroporous structure. The bead is about ten to one hundred-fifty microns in average diameter depending upon the rate of agitation employed during the process.

Example III illustrates a process for the production of beads by suspension polymerization in which an organic ester is entrapped "in situ" within the beads.

EXAMPLE III

Figure 4:
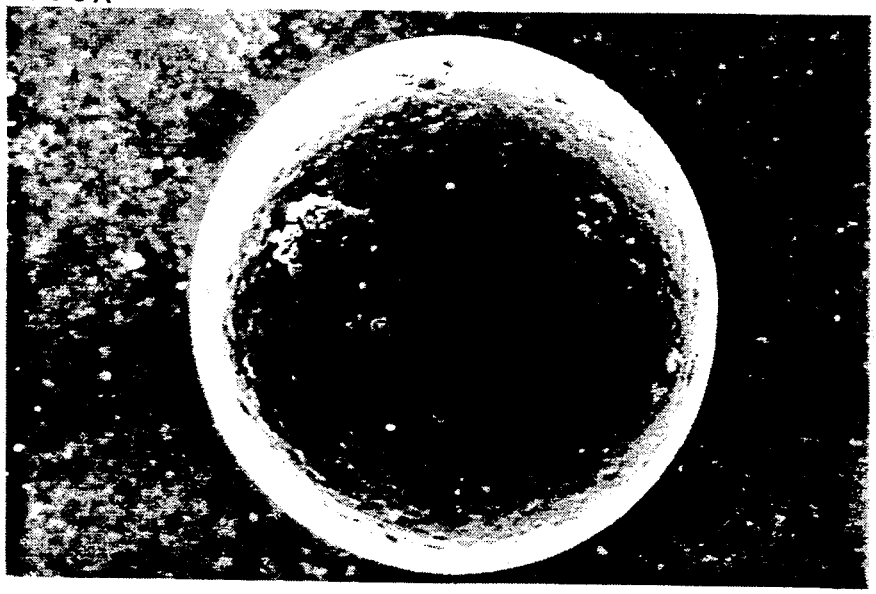
FIG. 4 is a photomicrograph of a single polymer bead produced by the suspension polymerization process of Example III.
Figure 5:
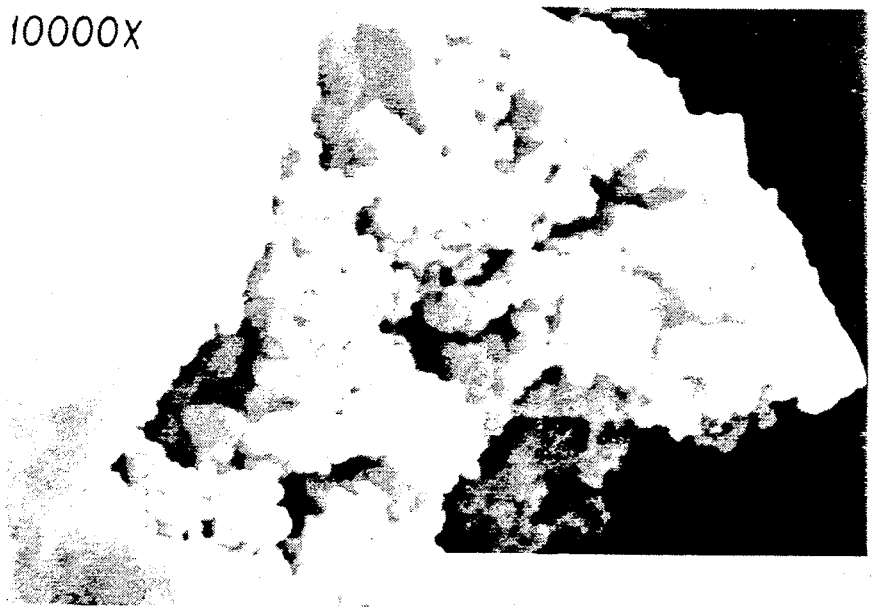
FIG. 5 is a photomicrograph of the bead of FIG. 4 but on an increased scale. The bead has a portion of its porous outer layer removed to reveal the interior macroporous structure of the bead.

Into a two liter three necked flask equipped with a stirrer, thermometer and a nitrogen purge 1.2 grams of polyvinyl pyrrolidone was dissolved in 1500 milliliters of water. A solution of 335 grams of 2-ethylhexyl oxystearate ester, 132 grams of ethylene glycol dimethacrylate, thirty-three grams of 2-ethylhexyl methacrylate and five milliliters of t-butyl peroctoate was bubbled with nitrogen for five minutes. This mixture was slowly added to the stirred aqueous solution of polyvinyl pyrrolidone at twenty-two degrees Centigrade under nitrogen purge. The temperature was raised to eighty degrees with constant agitation and maintained for fifteen minutes until polymerization initiated. The temperature remained at eighty degrees for an additional two hours to complete the reaction. White beads were collected by filtering off supernatant liquid and the beads were dried to remove any excess water. The beads weighed 450 grams providing a yield of ninety percent and were 0.25 to 0.5 millimeters in average diameter. Beads of this type are shown in FIGS. 4 and 5. Other protective colloids such as starch, polyvinyl alcohol, carboxymethyl cellulose, methyl cellulose or inorganic divalent alkali metal hydroxides such as MgOH may be used in place of polyvinyl pyrrolidone.

In Example III macroporous polymers submicron in size are produced and polymerization is conducted in the presence of an active ingredient which does not dissolve or swell the resulting polymer. The monomers and the active ingredient are mutually soluble but insoluble in the aqueous suspending medium in which droplets are formed. Polymerization occurs within the suspended droplets and beads or spheres are produced. The active ingredient which is polymerized "in situ" is entrapped and contained within the beads but the active ingredient is capable of being released. A volatile solvent or porogen can be substituted for the active ingredient and removed leaving an empty porous polymer bead product free of "in situ" entrapped active materials.

Examples of polyunsaturated monomers which may be employed are ethylene glycol dimethacrylate, triethylene glycol dimethacrylate, tetraethylene glycol dimethacrylate, trimethylolpropane ethoxylated triacrylate, ditrimethylolpropane dimethacrylate; propylene, dipropylene and higher propylene glycols; 1,3 butylene glycol dimethacrylate; 1,4 butanediol dimethacrylate; 1,6 hexanediol dimethacrylate, neopentyl glycol dimethacrylate, pentaerythritol dimethacrylate, dipentaerythritol dimethacrylate, bisphenol A dimethacrylate, divinyl and trivinylbenzene, divinyl and trivinyltoluene, triallyl maleate, triallyl phosphate, diallyl maleate, and diallyl itaconate.

Monounsaturated monomers include methacrylates and acrylates having straight or branched chain alkyl groups with 1 to 30 carbon atoms preferably 5 to 18 carbon atoms. Preferred monomers are lauryl methacrylate, 2-ethylhexyl methacrylate, isodecylmethacrylate, stearyl methacrylate, hydroxyethyl methacrylate, hydroxypropyl methacrylate, diacetone acrylamide, phenoxyethyl methacrylate, tetrahydrofurfuryl methacrylate and methoxyethyl methacrylate. Additional suitable monomers can be found in many of the patents referred to in the Background section. Highly crosslinked polymeric systems consisting of particles of submicron size can be prepared from only monomers having at least two polymerizable unsaturated bonds and containing no comonomers having monounsaturated moiety as taught in U.S. Pat. No. 4,962,170.

Removal of some entrapped ingredients has been accomplished surprisingly by mechanical means utilizing an unexpected phenomenon of the adsorbent that the powder material, while being shear sensitive, is not compressive sensitive. Thus it has been possible to apply compressive forces generated by a pair of stainless steel surfaces to the laden adsorbent powder to squeeze out and remove an active entrapped ingredient. The compressive forces have not been found to cause a degenerative effect upon the resulting adsorbent powder. During laboratory assimilations of compressive forces utilizing two stainless steel disks and a vice, the powder adsorbent has been sifted to break up any compacted powder masses followed by squeezing out of the entrapped active ingredient.

The volatile low viscosity organosilicon compound contemplated in accordance with the present invention includes cyclic silicone fluids and linear silicones. Representative of these materials are polydimethylcyclosiloxane and hexamethyldisiloxane. Such fluids have viscosities of 0.65 to 5.0 centistokes measured at twenty-five degrees Centigrade.

The volatile cyclic silicones generally conform to the formula $(R_2SiO)_x$ in which R is an alkyl radical having from one to three carbon atoms or a phenyl group. Most typically the cyclic siloxanes have the formula $[(CH_3)_2SiO]_x$ in which x is an integer from three to ten. Some volatile cyclic siloxane compounds found to be especially useful in accordance with the present invention are the tetramer compound octamethylcyclotetrasiloxane and the pentamer compound decamethylcyclopentasiloxane. Mixtures of the tetramer and pentamer may also be employed. Such cyclic siloxanes have viscosities ranging from about 2.5 centistokes to about five centistokes. These materials are also known under The Cosmetics, Toiletries and Fragrance Association designation as cyclomethicone.

The volatile low viscosity linear silicone fluids have the formula $R_3SiO(R_2SiO)_nSiR_3$ in which R is an alkyl radical having one to six carbon atoms and n is an integer of from two to nine. Most representative of this class of linear siloxane is hexamethyldisiloxane of the formula

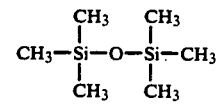

which has a viscosity of 0.65 centistokes measured at twenty-five degrees Centigrade.

Both the cyclic and linear low viscosity volatile silicones are clear fluids and are essentially odorless, nontoxic, nongreasy and nonstinging. Cosmetically they are nonirritating to the skin and possess the properties of good spreadability and ease of rub-out. The materials evaporate leaving behind no residue.

The antimicrobial agent which is most suitable is an antibacterial compound such as benzoyl peroxide, salicyclic acid or resorcinol which are known for their ability to alleviate the acne problem to one degree or another. The mixture of the antimicrobial agent and the volatile low viscosity organosilicon compound should preferably be in the weight ratio of 50:50 to 70:30 antimicrobial agent to organosilicon compound. The following additional examples illustrate the skin treatment method and composition contemplated in accordance with the present invention.

EXAMPLE IV

Forty weight percent of benzoyl peroxide and forty weight percent of volatile cyclic silicone were combined. The volatile cyclic silicone was a mixture of the tetramer compound octamethylcyclotetrasiloxane and the pentamer compound decamethylcyclopentasiloxane. The mixture of the tetramer and pentamer had a viscosity of five centistokes and included seventy-five percent of the tetramer and twenty-five percent of the pentamer. The benzoyl peroxide and volatile cyclic silicone mixture was ground with a mortar and pestle until a suspension of finely dispersed benzoyl peroxide was produced. The benzoyl peroxide suspension was combined and blended with twenty weight percent of the macroporous polymer powder of Example I until there was produced a uniform free flowing powder. The free flowing powder was applied to the facial skin of volunteers. Following the elapse of thirty to sixty minutes after the application of the free flowing powder, a very slight whiteness was noted to appear on the skin.

The volunteers indicated that the free flowing powder had rubbed out smoothly and easily onto the skin. The test site on the skin of the volunteers remained non-oily for upwards of three hours following application of the free flowing powder indicating that as the volatile cyclic silicone evaporated and as the antimicrobial agent was slowly released from the free flowing powder, excess oil produced by the skin was adsorbed by the macroporous polymer powder which remained on the skin. This is significant in that acne treatment is enhanced by prevention of buildup on the skin of excess sebum. The presence of the volatile cyclic silicone additionally contributes the benefit of enabling a cosmetically acceptable product to be formulated and provides the characteristic good spreadability and ease of rubout of the formulation. A dry silky feel is left to the skin as the volatile cyclic silicone evaporates. Unlike organic volatile carrier materials, the volatile cyclic silicones do not cool the skin as they evaporate.

While European application 306236 published Mar. 8, 1989 refers to porous beads containing benzoyl peroxide or salicylic acid, it does not disclose the combination with a volatile cyclic silicone and the attendant benefits of employing the silicones as noted above.

EXAMPLE V

Example IV was repeated except that salicyclic acid was used as the antimicrobial agent. The results were the same as indicated in Example IV.

EXAMPLE VI

Example IV was repeated except that fifty-five weight percent of benzoyl peroxide and twenty-five weight percent of the volatile cyclic silicone were employed. The results were the same as indicated in Example IV.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations of the scope on the present invention.

That which is claimed:

1. A method of treating skin disorders comprising (I) applying topically to the skin a mixture of an antimicrobial agent and a volatile low viscosity organosilicon compound, the mixture being entrapped within and dispersed uniformly throughout discrete particles of a hydrophobic macroporous highly crosslinked polymer, (II) spreading the particles on the skin in order to release the mixture, (III) allowing the volatile low viscosity organosilicon compound to evaporate and, (IV) adsorbing oil from the skin into the macroporous polymer, the mixture of the antimicrobial agent and the volatile low viscosity organosilicon compound being in the weight ratio of 50:50 to 70:30 antimicrobial agent to organosilicon compound.

2. The method of claim 1 in which the antimicrobial agent is an antibacterial compound selected from the group consisting of benzoyl peroxide, salicylic acid and resorcinol.

3. The method of claim 1 in which the volatile low viscosity organosilicon compound is selected from the group consisting of cyclic silicone fluids and linear silicone fluids.

4. The method of claim 1 in which the volatile low viscosity organosilicon compound is selected from the group consisting of volatile cyclic silicones having the formula $(R_2SiO)_x$ in which R is an alkyl radical having from one to three carbon atoms or a phenyl group, and x is an integer from three to ten, and linear silicone fluids have the formula $R_3SiO(R_2SiO)_nSiR_3$ in which R is an alkyl radical having one to six carbon atoms and n is an integer of from two to nine.

5. The method of claim 1 wherein the polymer particles are formed from at least one polyunsaturated monomer.

6. The method of claim 5 wherein the polyunsaturated monomer is selected from the group consisting of ethylene glycol dimethacrylate and tetraethylene glycol dimethacrylate.

7. The method of claim 1 wherein the polymer particles are formed from at least one monounsaturated monomer and at least one polyunsaturated monomer.

8. The method of claim 7 wherein the monounsaturated monomer is selected from the group consisting of lauryl methacrylate and 2-ethylhexyl methacrylate, and the polyunsaturated monomer is selected from the group consisting of ethylene glycol dimethacrylate and tetraethylene glycol dimethacrylate.

9. The method of claim 1 in which the macroporous polymer particles are in the form of a powder, the powder being a combined system of particles, the system of powder particles including unit particles of less than about one micron in average diameter, agglomerates of fused unit particles of sizes in the range of about twenty to eighty microns in average diameter, and aggregates of clusters of fused agglomerates of sizes in the range of about two-hundred to about twelve-hundred microns in average diameter.

10. The method of claim 9 in which the polymer is a polymethacrylate.

11. A composition comprising a mixture of an antimicrobial agent and a volatile low viscosity organosilicon compound, the mixture being entrapped within and dispersed uniformly throughout discrete particles of a hydrophobic macroporous highly crosslinked polymer, the mixture of the antimicrobial agent and the volatile low viscosity organosilicon compound being in the weight ratio of 50:50 to 70:30 antimicrobial agent to organosilicon compound.

12. The composition of claim 11 in which the antimicrobial agent is an antibacterial compound selected from the group consisting of benzoyl peroxide, salicylic acid and resorcinol.

13. The composition of claim 11 in which the volatile low viscosity organosilicon compound is selected from the group consisting of cyclic silicone fluids and linear silicone fluids.

14. The composition of claim 11 in which the volatile low viscosity organosilicon compound is selected from the group consisting of volatile cyclic silicones having the formula $(R_2SiO)_x$ in which R is an alkyl radical having from one to three carbons atoms or a phenyl group, and x is an integer from three to ten, and linear silicone fluids having the formula $R_3SiO(R_2SiO)_nSiR_3$ in which R is an alkyl radical having one to six carbon atoms and n is an integer of from two to nine.

15. The composition of claim 11 wherein the polymer particles are formed from at least one polyunsaturated monomer.

16. The composition of claim 15 wherein the polyunsaturated monomer is selected from the group consisting of ethylene glycol dimethacrylate and tetraethylene glycol dimethacrylate.

17. The composition of claim 11 wherein the polymer particles are formed from at least one monounsaturated monomer and at least one polyunsaturated monomer.

18. The composition of claim 17 wherein the monounsaturated monomer is selected from the group consisting of lauryl methacrylate and 2-ethylhexyl methacrylate, and the polyunsaturated monomer is selected from the group consisting of ethylene glycol dimethacrylate and tetraethylene glycol dimethacrylate.

19. The composition of claim 11 in which the macroporous polymer particles are in the form of a powder, the powder being a combined system of particles, the system of powder particles including unit particles of less than about one micron in average diameter, agglomerates of fused unit particles of sizes in the range of about twenty to eighty microns in average diameter, and aggregates of clusters of fused agglomerates of sizes in the range of about two-hundred to about twelve-hundred microns in average diameter.

20. The composition of claim 19 in which the polymer is a polyethacrylate.

* * * * *